(12) United States Patent
Vaillant et al.

(10) Patent No.: US 8,685,087 B2
(45) Date of Patent: Apr. 1, 2014

(54) INTRAOCULAR LENS AND METHOD OF MAKING AN INTRAOCULAR LENS

(75) Inventors: Yann Vaillant, Toulouse (FR); Benoit Bessiere, Dremil Lafage (FR)

(73) Assignee: Bausch & Lomb Incorporated, Rochester, NY (US)

( * ) Notice: Subject to any disclaimer, the term of this patent is extended or adjusted under 35 U.S.C. 154(b) by 1232 days.

(21) Appl. No.: 12/332,643

(22) Filed: Dec. 11, 2008

(65) Prior Publication Data
US 2010/0152846 A1   Jun. 17, 2010

(51) Int. Cl.
*A61F 2/14* (2006.01)

(52) U.S. Cl.
USPC .......................... 623/6.12; 623/6.46

(58) Field of Classification Search
USPC .................. 623/6.38–6.55; 606/107
See application file for complete search history.

(56) References Cited

U.S. PATENT DOCUMENTS

| | | |
|---|---|---|
| 4,087,866 A | 5/1978 | Choyce et al. |
| 4,122,556 A | 10/1978 | Poler |
| 4,277,852 A | 7/1981 | Poler |
| 4,316,291 A | 2/1982 | Severin |
| 4,409,690 A | 10/1983 | Gess |
| 4,426,741 A | 1/1984 | Bittner |
| 4,490,860 A | 1/1985 | Rainin |
| 4,536,897 A | 8/1985 | Powell |
| 4,562,600 A | 1/1986 | Ginsberg et al. |
| 4,601,721 A | 7/1986 | Kamerling |
| 4,629,461 A | 12/1986 | Clayman et al. |
| 4,990,159 A | 2/1991 | Kraff |
| 5,092,880 A | 3/1992 | Ohmi |
| 5,928,282 A | 7/1999 | Nigam |
| 6,183,513 B1 | 2/2001 | Guenthner et al. |
| 6,190,410 B1 | 2/2001 | Lamielle et al. |
| 6,200,344 B1 | 3/2001 | Lamielle et al. |
| 6,336,932 B1 | 1/2002 | Figueroa et al. |
| 6,371,960 B2 | 4/2002 | Heyman et al. |
| 6,398,809 B1 | 6/2002 | Hoffmann et al. |
| 6,461,384 B1 | 10/2002 | Hoffmann et al. |
| 6,468,307 B1 | 10/2002 | Baikoff et al. |
| 6,471,708 B2 | 10/2002 | Green |
| 6,558,419 B1 | 5/2003 | Pham et al. |
| 6,629,979 B1 | 10/2003 | Feingold |
| 2001/0051825 A1* | 12/2001 | Peterson ..................... 623/6.12 |
| 2003/0158560 A1 | 8/2003 | Portney |

(Continued)

FOREIGN PATENT DOCUMENTS

| | | |
|---|---|---|
| EP | 0261186 B1 | 6/1991 |
| EP | 1 882 461 A1 | 1/2008 |
| WO | WO 01/15779 A1 | 3/2001 |
| WO | WO 2008/036674 A1 | 3/2008 |

OTHER PUBLICATIONS

International Search Report (PCTISA/210) and Written Opinion (PCT/ISA/237) mailed on Sep. 30, 2010.

*Primary Examiner* — David Isabella
*Assistant Examiner* — Joshua Levine
(74) *Attorney, Agent, or Firm* — Jeffrey B. Powers

(57) ABSTRACT

In a first aspect, the invention provides an IOL having an optic with a peripheral section including one or more visually observable markers formed on the optic peripheral section and located within the visually observable zone of a surgeon viewing the IOL in the implanted condition through the pupil. In a second aspect of the invention, the IOL peripheral section includes an edge provided with a plunger engagement segment configured to inhibit off-axis movement of a plunger tip when engaged therewith.

12 Claims, 4 Drawing Sheets

(56) References Cited

U.S. PATENT DOCUMENTS

| | | |
|---|---|---|
| 2004/0156013 A1 | 8/2004 | Lindacher et al. |
| 2005/0149184 A1 | 7/2005 | Bogaert |
| 2005/0288785 A1 | 12/2005 | Portney |
| 2006/0089712 A1 | 4/2006 | Malecaze |
| 2007/0027539 A1* | 2/2007 | Pynson .................. 623/6.16 |
| 2008/0183289 A1 | 7/2008 | Werblin |

* cited by examiner

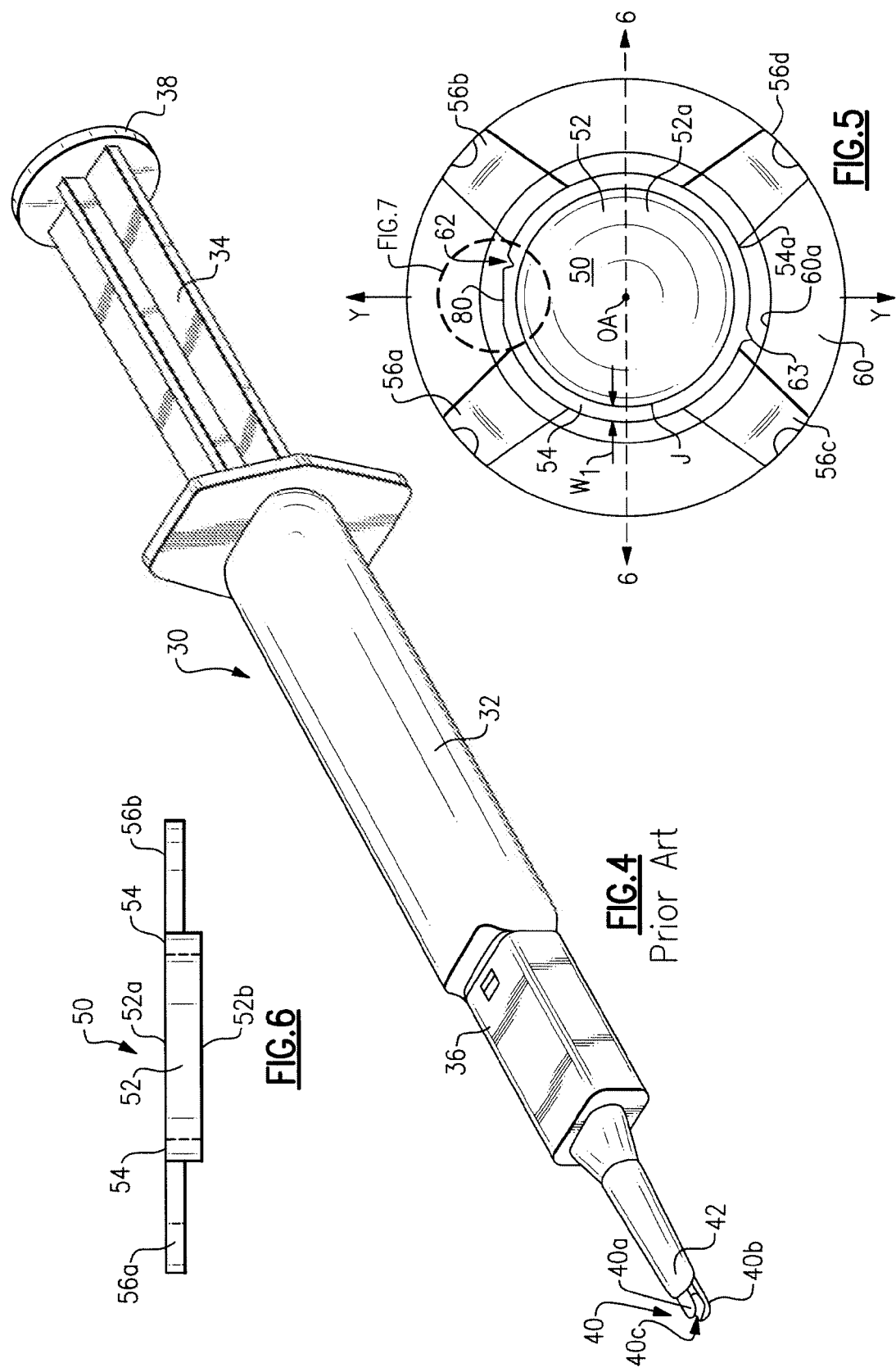

INTRAOCULAR LENS AND METHOD OF MAKING AN INTRAOCULAR LENS

BACKGROUND OF THE INVENTION

The present invention relates to intraocular lenses. In a first aspect, the invention more particularly relates to an intraocular lens ("IOL") having a visually observable inversion marker formed on a peripheral section of the optic. The visually observable inversion marker may be seen through an appropriate ophthalmic viewing instrument such as a slit lamp or a binocular microscope during surgery, for example, to aid a surgeon or other practitioner in confirming proper orientation of the IOL within a patient's eye. In a second aspect, the invention provides an IOL having a plunger engagement segment formed on the optic peripheral edge. The plunger engagement segment is configured to inhibit off-axis movement of the IOL relative to a plunger tip when engaged therewith and advanced to inject the IOL into an eye.

IOLs are well known and are used for implanting into an eye to replace the eye's extracted natural lens in a common surgical procedure known as cataract surgery. There are many different types of IOLs available and the surgeon chooses the IOL according to one or more factors including, for example, the physiology and refractive needs of the patient's eye. IOLs are configured with an optic and one or more haptics extending from the optic which act as anchoring elements to properly position the IOL within the eye. The IOL is implanted in the eye with the optic aligned along the eye's visual axis. The IOL may be implanted in a variety of locations within the eye, but typically is positioned within the capsular bag from which the natural lens has been extracted.

The IOL optic typically has a circular peripheral edge with opposite anterior and posterior surfaces. When implanted into an eye, the anterior surface faces toward the pupil and the posterior surface faces toward the retina at the back of the eye. Unless the anterior and posterior surfaces are of the same optical configuration (e.g., symmetrically biconvex), it is important to ensure the anterior surface faces toward the pupil when the IOL is implanted in the eye. For some IOL designs, and in particular IOL designs bilaterally symmetrically disposed about an axis extending perpendicularly through the lens' optical axis, it may be difficult to visually ascertain which surface is the anterior surface and which is the posterior surface. Visually observable inversion markers have thus been provided in prior art IOLs to aid the surgeon in identifying the anterior from the posterior surface of the IOL prior to implantation. For example, as seen in FIG. 1, a prior art IOL 10 is provided having an optic 12 and four haptics 14a-d with a visually observable inversion marker in the form of protrusions 16a,b formed on the haptics 14a and 14c, respectively. Absent protrusions 16a,b, IOL 10 is bilaterally symmetrical about axis X-X extending perpendicularly through optical axis OA and would therefore appear substantially the same when viewed from either the posterior or anterior facing surfaces thereof. Although not shown, instructions would be provided with the IOL 10 instructing the surgeon that the anterior surface is identified when the haptics having the protrusions have their respective lobes 14a', 14c' extending in a clockwise direction. As such, prior to implantation and upon viewing the haptics, the surgeon may readily distinguish between the anterior and posterior surfaces. However, once the IOL 10 has been implanted in an eye, surrounding structures of the eye, such as iris 18, may obstruct viewing the haptics 14a-d since the haptics are located posteriorly of iris 18. As such, it is difficult, if not impossible, for a surgeon to confirm whether or not the IOL 10 has been implanted with the anterior surface thereof facing the pupil as required. If the IOL has been inverted with the anterior surface thereof facing the retina rather than the pupil, the IOL will not function properly and must be removed and replaced. There therefore remains a need for an IOL having a visually observable inversion marker which is visually observable to the surgeon after the IOL has been implanted into an eye.

An IOL is implanted in an eye with the aid of an implantation tool such as an IOL injector having a main body portion with a lumen and a plunger telescoping within the lumen. The IOL is placed inside the lumen and the injector tip is inserted into an incision made in the eye. The plunger is then advanced with the plunger tip engaging and pushing the IOL out of the injector and into the eye. The plunger tip may be bifurcated with spaced prongs forming a slot to capture the IOL optic peripheral edge therebetween. Since the IOL optic periphery is typically circular, the plunger tip may unintentionally slip and/or move in an off-axis manner during IOL delivery, particularly once the IOL and plunger tip have exited the lumen. There therefore remains a need for an IOL having a plunger engagement segment which inhibits off-axis movement of the plunger tip relative to the IOL.

SUMMARY OF THE INVENTION

In a first aspect, the present invention addresses, in one or more embodiments thereof, the first need by providing an IOL having an optic with a peripheral section including one or more visually observable inversion markers formed on the optic peripheral section and located within the visually observable zone of a surgeon viewing the IOL in the implanted condition through the pupil.

In a second aspect, the present invention addresses, in one or more embodiments thereof, the second need by providing an IOL having a plunger engagement segment formed on the optic peripheral edge. The plunger engagement segment is configured to inhibit off-axis movement of a plunger tip relative to the IOL optic when engaged therewith. In one embodiment, the plunger engagement segment is formed as a substantially straight edge. In an alternate embodiment, the plunger engagement segment is a recess formed in the optic peripheral edge. In yet another embodiment, the plunger engagement segment is formed between two protrusions formed on the optic peripheral edge. In still a further embodiment, the visually observable inversion marker is formed within the plunger engagement segment. In still a further embodiment, the plunger engagement segment also acts as the visually observable inversion marker.

BRIEF DESCRIPTION OF THE DRAWING

FIG. 4 is a perspective view of a prior art IOL injector;

FIG. 5 is a plan view of an embodiment of the inventive IOL relative to an iris diagrammatically shown as viewed by a surgeon in the implanted condition;

FIG. 6 is a cross-sectional view of an embodiment of the inventive IOL as taken generally along the line 6-6 of FIG. 5;

DETAILED DESCRIPTION

Figure 1:
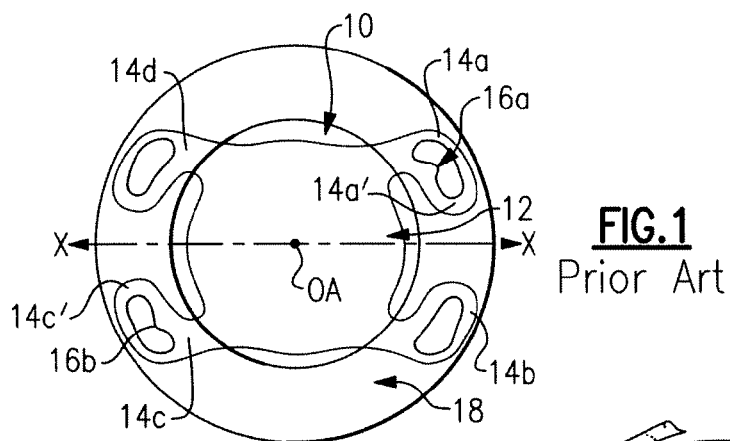
FIG. 1 is a plan view of a prior art IOL relative to an iris diagrammatically shown as viewed by a surgeon in the implanted condition.
Figure 2:
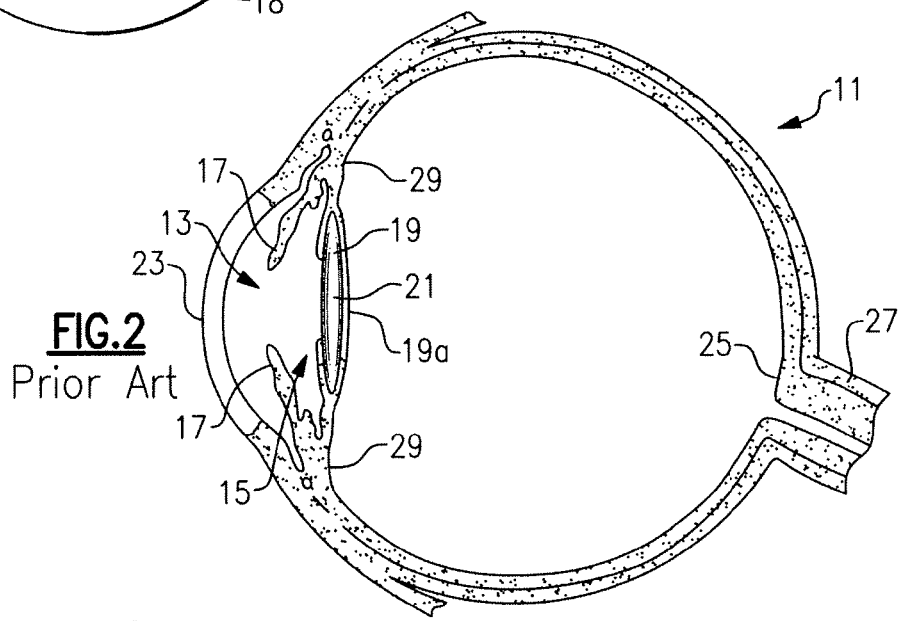
FIG. 2 is a cross-sectional view of a human eye showing the natural lens within the capsular bag of the eye.

Referring now to the drawing, there is seen in FIG. 2 a cross-sectional view of a human eye 11 having an anterior chamber 13 and a posterior chamber 15 separated by the iris 17. Within the posterior chamber 15 is a capsule 19 which holds the eye's natural crystalline lens 21. Light enters the eye by passing through the cornea 23 to the crystalline lens 21 which act together to direct and focus the light upon the retina 25 located at the back of the eye. The retina connects to the optic nerve 27 which transmits the image received by the retina to the brain for interpretation of the image.

Figure 3:
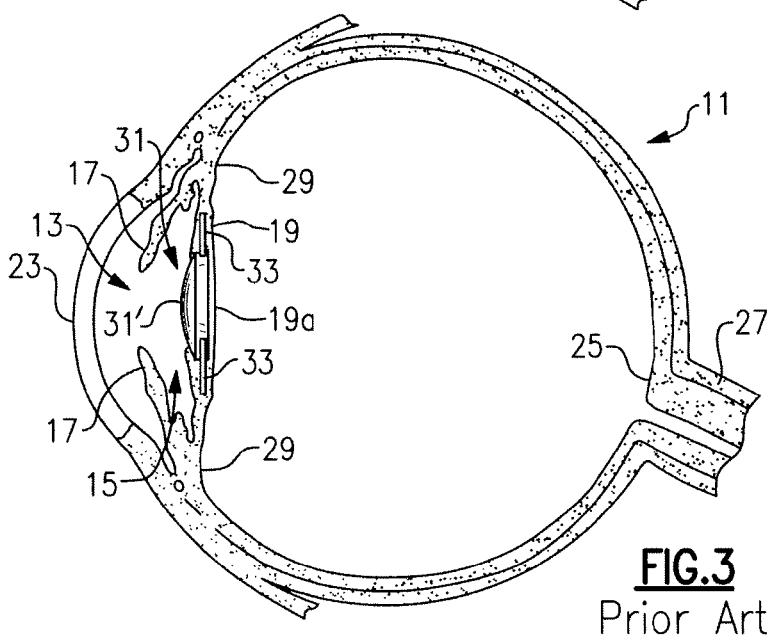
FIG. 3 is a cross-sectional view of a human eye showing the natural lens removed and replaced with an IOL.

In an eye where the natural crystalline lens has been damaged (e.g., clouded by cataracts), the natural lens is no longer able to properly focus and direct incoming light to the retina and images become blurred. A well known surgical technique to remedy this situation involves removal of the damaged crystalline lens which may be replaced with an artificial lens known as an intraocular lens or IOL such as prior art IOL 31 seen in FIG. 3. Although there are many different IOL designs as well as many different options as to exact placement of an IOL within an eye, the most common surgery places the IOL inside the substantially ovoid-shaped capsule 19 which is located behind the iris 17 in the posterior chamber 15 of the eye 11. In this surgical technique, a part of the anterior portion of the capsular bag is cut away (termed a "capsularhexis") while leaving the posterior capsule 19a intact and still secured to the ciliary body 29.

An IOL includes a central optic portion 31' which simulates the extracted natural lens by directing and focusing light upon the retina, and further includes means for securing the optic in proper position within the capsular bag. A common IOL structure for securing the optic is called a haptic which is a resilient structure extending outwardly from the peripheral edge of the optic. In a particularly common IOL design, two or more haptics 33 extend from opposite sides of the optic and provide a biasing force against the inside of the capsule which secures the optic in the proper position within the capsule (see FIG. 3).

An IOL is implanted in an eye by a surgeon with the aid of an injector tool such as prior art IOL injector tool 30 seen in FIG. 4. Tool 30 includes a tubular body portion 32 and a plunger 34 which telescopes within tubular body portion 32. The flexible IOL is placed inside the IOL loading chamber 36 and the plunger is advanced by pressing on end 38 in the manner of a syringe. The plunger tip 40 is bifurcated and includes first and second spaced prongs 40a, 40b which define a slot 40c in which the optic peripheral edge may extend. With the injector tip 42 inserted into the patient's eye, the surgeon advances the plunger 34 with the plunger tip 40 pushing and compressing the IOL through and out the narrowing injector tip 42 and into the patient's eye. It is understood that prior art injector tool 30 is shown and described herein for purpose of background only and as such, the invention is not to be limited thereby.

Referring now to FIGS. 5 and 6, an embodiment of invention is shown as an IOL 50 having an optic 52 surrounded by a peripheral section 54 having a peripheral section edge 54a with four haptics 56a-56d extending from peripheral section edge 54a. It is understood that IOL 50 may have any number and configuration of haptics and is not limited to the embodiment shown and described herein. Peripheral section 54 is typically homogeneously formed with optic 52 and may or may not be visually distinguishable therefrom. That is, in some IOL designs, peripheral section 54 may blend seamlessly with optic 52 while in other designs there may be a clear visual line indicating the juncture "J" of optic 52 with peripheral section 54. Irrespective of the particular IOL design, peripheral section 54 is not configured to be an optical part of the implanted IOL 50 and as such does not appreciably contribute to the optical functioning thereof.

FIG. 5 shows a diagrammatic representation of an IOL 50 implanted in an eye. Upon successful implantation of IOL 50, optic 52, including peripheral section 54, is clearly visible through the pupil defined by iris 60 while a majority of haptics 56a-56d are hidden behind iris 60. Optic 52 and peripheral section 54 may thus be seen through the patient's pupil (most commonly in the 4-8 mm diameter range) using appropriate ophthalmic viewing instruments such as a slit lamp or a binocular microscope during surgery, for example.

As mentioned in the Background section hereof, the anterior and posterior optic surfaces of IOL 50 may be different such that it is important for the surgeon to ensure the anterior surface is facing the eye's pupil while the posterior surface is facing the eye's retina. For example, optic anterior surface 52a may be aspheric while posterior surface 52b is planar. Should the surgeon inadvertently implant IOL 50 in an inverted position with posterior surface 52b facing the pupil and anterior surface 52a facing the retina, the optics of IOL 50 would not function properly and the patient would not be able to see correctly. Furthermore, the barrier edge surrounding the posterior surface 52b of the optic 52 would not be in position to press into the posterior wall of the capsular bag as intended. As is well known in the art, the barrier edge functions to prevent lens epithelial cells (LECs) from migrating between the posterior capsular wall and the posterior surface of the lens, a condition known as posterior capsular opacification (PCO) or "secondary cataract". Should this occur, the patient would require a further surgical procedure to remove the posterior capsular wall. Thus, should the surgeon inadvertently implant an IOL in an inverted position, the surgeon would have to remove the IOL 50 and replace it with an IOL in the correct, non-inverted position.

Referring again to FIG. 5, an embodiment of the present invention includes a visually observable inversion marker 62 formed on peripheral section 54. Since peripheral section 54 is within the boundary of the opening defined by iris 60, inversion marker 62 may be seen by a surgeon through an appropriate ophthalmic viewing instrument. In one embodiment, inversion marker 62 is formed within a radial distance of 4 mm of optical axis OA. In another embodiment, inversion marker 62 is formed within a radial distance of 3 mm of optical axis OA. In yet another embodiment, inversion marker 62 is formed within a radial distance of 2 mm of optical axis OA. In an alternate embodiment, inversion marker 62 is formed on at least one haptic 56a-56d and disposed so as to be visually observable through the pupil when IOL 50 is implanted in an eye. Marker 62 is positioned in a manner creating bilateral asymmetry along axis Y-Y extending perpendicularly through optical axis OA. Without marker 62, IOL 50 is bilaterally symmetrical about axis Y-Y. Marker 62 thus forms an asymmetry matched to the anterior and posterior surfaces 52*a*, 52*b* whereby the anterior surface may be readily identified. In the embodiment and view of FIG. 5, anterior surface 52*a* is facing the viewer and the marker 62 is positioned to the left of the closest haptic 56*b*. If the IOL 50 were inverted and the posterior surface was facing the viewer, marker 62 would appear to the right of haptic 56*b*. Instructions may therefore be provided with IOL 50 that the anterior surface 52*a* may be identified when the marker 62 is located to the left of the closest haptic. It will thus be appreciated that the surgeon may readily identify and distinguish between the anterior and posterior surfaces when viewing the implanted IOL 50 through an appropriate ophthalmic viewing instrument. Should the IOL have been implanted in an inverted position, this may be immediately known and rectified rather than finding out after conclusion of the operation and the patient's follow-up eye test.

The visually observable inversion marker may be of any desired type and configuration so long as it is visually observable as described herein. For example, rather than a recess as shown in FIG. 5, the marker may comprise a protrusion extending out from peripheral section edge 54*a* or a color, hash mark, manufacturer's logo or other marking or any combination thereof may be formed on or into the surface of peripheral section 54 and/or peripheral section edge 54*a*. The exact placement of marker 62 along peripheral section 54 and/or peripheral section edge 54*a* may also vary although if the IOL is of a symmetrical design, marker 62 should of course be positioned to create asymmetry as in the embodiment shown in FIG. 5. Also, more than one marker 62 may be used on a single IOL if desired. For example, a second marker 63 may be positioned diametrically opposite first marker 62 adjacent haptic 56*c*. Additional markers such as second marker 63 may be of the same or different type as first marker 62. In the embodiment shown in FIG. 5, second marker 63 is in the form of a protrusion extending from peripheral section edge 54*a*.

Figure 11A:
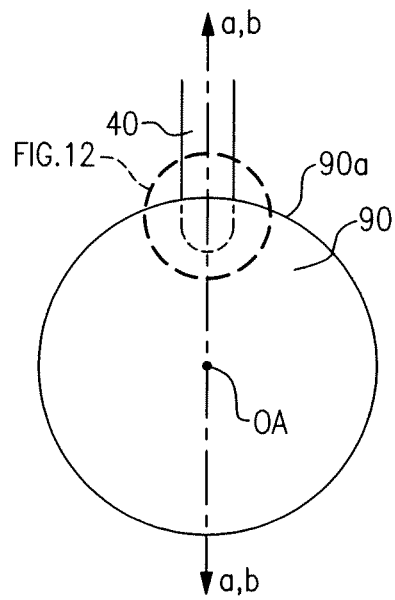
FIG. 11A is a plan view of a plunger tip engaging an IOL optic in the intended manner.
Figure 11B:
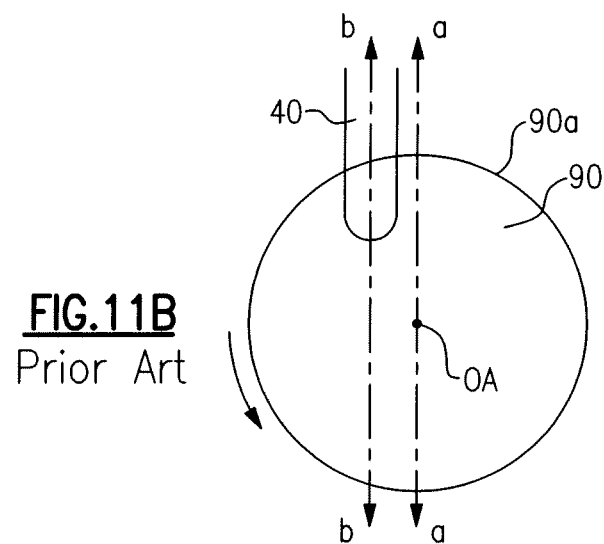
FIG. 11B is the view of FIG. 11A showing the IOL optic translated to an off-axis position relative to the plunger tip.
Figure 12:
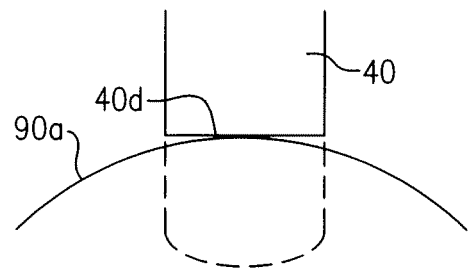
FIG. 12 is an enlarged view of the portion inside the detail circle labeled FIG. 12 in FIG. 11A.

Attention is now turned to a second aspect of the invention comprising a plunger engagement segment adapted for engagement with a plunger tip used to inject IOL 50 into an eye. A typical prior art plunger tip 40 is seen in FIG. 4 to include a bifurcated tip having prongs 40*a* and 40*b* defining a slot 40*c* therebetween. As is known in the art, an IOL is loaded into the injector and the plunger is advanced which captures the IOL optic within slot 40*c*. Further advancement of the plunger pushes and compresses the IOL through the narrowing injector tip 42, eventually expressing the IOL therefrom and into an eye. Since a typical IOL optic periphery is circular, occasionally the plunger tip may slip or translate relative to the optic periphery. This phenomenon is illustrated in FIGS. 11A (non-slipped) and 11B (slipped). In FIG. 11A, an IOL optic 90 having a circular periphery 90*a* and an optical axis OA has an axis a-a extending perpendicularly through optical axis OA. Plunger tip 40 has a longitudinal axis b-b which is shown in FIG. 11A in axial alignment with axis a-a of optic 90 as intended. In FIG. 11B, the IOL 90 and plunger tip 40 have translated relative to each other relative to FIG. 11A such that plunger axis b-b is spaced from and thus no longer in axial alignment with optic axis a-a. FIG. 12 shows an enlarged view of the mismatched engagement surfaces of the plunger tip slot rear wall 40*d* which is substantially straight, and the IOL periphery 90*a* which is substantially circular. This mismatch between the engagement surfaces creates laterally unstable forces between the plunger tip and optic during plunger advancement occasionally resulting in unintended slippage therebetween. Any such slippage is undesirable since it can lead to improper positioning of the IOL within the eye and/or damage to the IOL itself.

Figure 7:
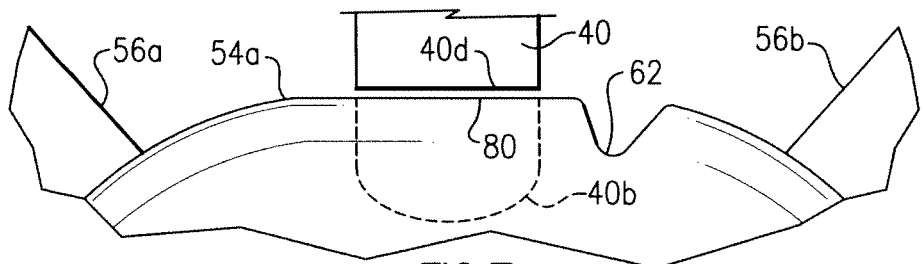
FIG. 7 is an enlarged view of the portion of the IOL inside the detail circle labeled FIG. 7 in FIG. 5.
Figure 8:
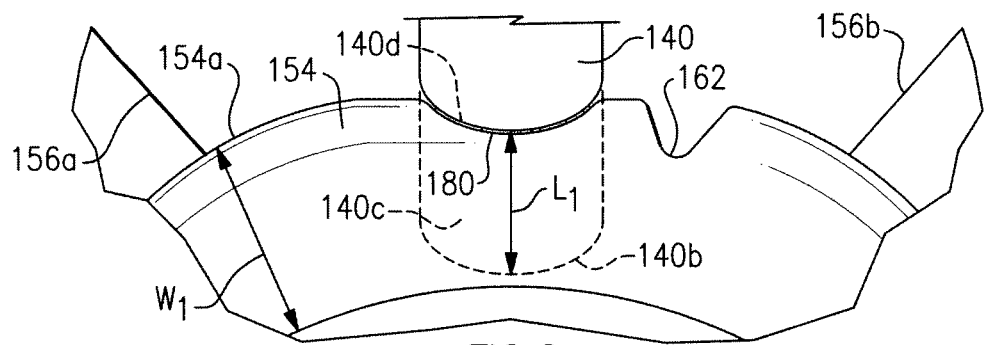
FIG. 8 is the view of FIG. 7 showing an alternate embodiment of the IOL with a plunger tip engaged therewith.
Figure 9:
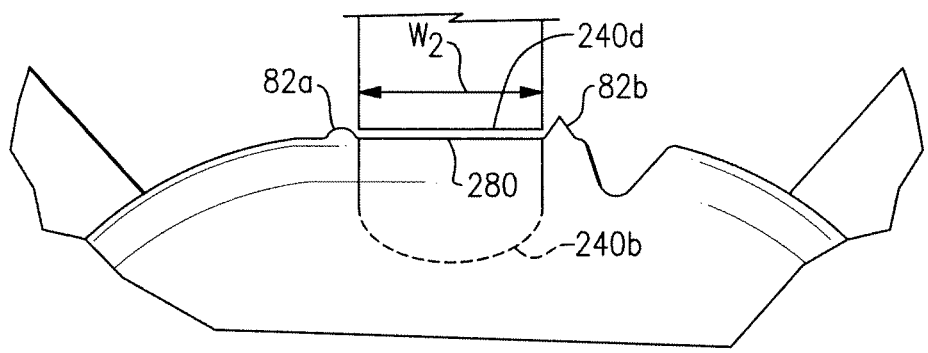
FIG. 9 is the view of FIG. 8. showing yet another alternate embodiment of the IOL.

As seen best in the enlarged detail view of FIG. 7, a substantially straight plunger engagement segment 80 is provided on optic peripheral edge 54*a* which matches the substantially straight plunger slot rear wall 40*d*. It is noted that in the views of FIGS. 7-9, the prongs which are located opposite prongs 40*b*, 140*b* and 240*b* are not shown for the sake of clarity. These two straight surfaces 80 and 40*b* in abutting engagement with each other create a laterally stable force profile therebetween and off-axis movement of the IOL relative to the plunger tip is thereby inhibited. Complimentary shapes between the engaging surfaces of the plunger tip and optic periphery other than straight are of course possible to create a more stable engagement force profile. For example, as seen in FIG. 8, a plunger slot rear wall 140*d* may be made convex while the plunger engagement segment 180 of the IOL optic peripheral edge 154*a* is formed in a complimentary concave shape. Of course the reverse shapes would be suitable as well, i.e., a concave plunger slot rear wall with a convex plunger engagement section. Other shapes and elements may be used to further enhance the stability between the plunger tip and IOL peripheral edge engagement surfaces. For example, as seen in FIG. 9, a pair of spaced protrusions 82*a* and 82*b* may be provided on either side of the plunger engagement segment 280 which may be straight as shown or curved. In this embodiment, the spacing between the protrusions 82*a* and 82*b* is slightly larger than the width $W_2$ of the plunger tip such that the protrusions provide lateral support to both sides of the plunger tip.

Protrusions 82*a*, 82*b* may be of the same shape or may have different shapes such as the rounded protrusion 82*a* and pointed protrusion 82*b* shown in FIG. 9. By providing different shapes to protrusions 82*a* and 82*b*, they may also serve the function of the visually observable inversion marker. It will thus be appreciated that the plunger engagement segment and the visually observable inversion marker may be combined.

Figure 10:
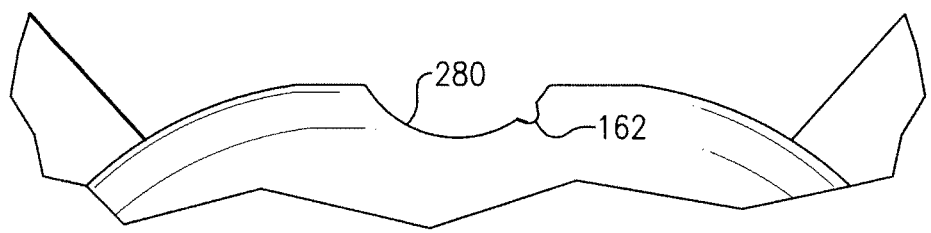
FIG. 10 is the view of FIG. 7 showing yet another alternate embodiment of the IOL.

FIG. 10 shows another embodiment of the invention wherein a visually observable inversion marker 162 is formed within plunger engagement segment 280. Although both engagement segment 280 and marker 162 are shown in FIG. 10 as concave, either may of course be any shape or type as described herein. Furthermore, IOLs manufactured in accordance with the present invention may form the visually observable inversion marker and plunger engagement segment in the same operation (e.g., molding, lathing, milling, etc.).

As seen in FIG. 8, it is preferred the length $L_1$ of slot 140*c* between the very tip of prong 140*a* and slot rear wall 140*d* is smaller than the width $W_1$ of peripheral section 154 such that the plunger tip does not reach far enough to touch and possibly damage the optic 50.

What is claimed is:

1. An intraocular lens comprising:
   a) an optic having an optical axis and a peripheral section;
   b) at least two haptics extending from said peripheral section, said haptics being bilaterally symmetrically disposed about an axis extending perpendicularly through said optical axis; and
   c) a visually observable inversion marker formed on one of said peripheral section and at least one of said haptics, said visually observable inversion marker being disposed so as to be visually observable through the pupil when said intraocular lens is implanted in an eye,
   wherein said peripheral section includes a plunger engagement segment comprising a substantially straight edge, and wherein said peripheral section includes an edge and said plunger engagement segment is formed between first and second protrusions formed on said peripheral section edge.

2. The intraocular lens of claim 1 wherein said peripheral section includes an edge and said visually observable inversion marker is a recess in said peripheral section edge.

3. The intraocular lens of claim 1 wherein said peripheral section includes an edge and said visually observable inversion marker is a protrusion extending outwardly from said peripheral section edge.

4. The intraocular lens of claim 1 in combination with an injector plunger having a tip with a slot and wherein said optic peripheral section has a width, said slot having a length which is smaller than said peripheral section width, said slot adapted to receive said peripheral section therein.

5. The intraocular lens of claim 4 wherein said peripheral section includes a plunger engagement segment and said plunger tip slot includes a rear wall, said plunger engagement segment and said plunger tip slot rear wall having complimentary shapes.

6. The intraocular lens of claim 1 wherein said peripheral section includes a plunger engagement segment and said visually observable inversion marker is formed on said plunger engagement segment.

7. The intraocular lens of claim 1 in combination with an injector plunger having a tip wherein said first and second protrusions are spaced apart a distance slightly larger than the width of said plunger tip.

8. The intraocular lens of claim 7 wherein said protrusions are of different shapes and comprise said visually observable inversion marker.

9. The intraocular lens of claim 1 wherein said peripheral section includes a plunger engagement segment positioned adjacent to said visually observable inversion marker.

10. The intraocular lens of claim 9 wherein said intraocular lens includes first, second, third and fourth haptics and said visually observable inversion marker and said plunger engagement segment are located between said first and second haptics.

11. The intraocular lens of claim 10 and further comprising a second visually observable inversion marker located on said peripheral section edge between said third and fourth haptics.

12. The intraocular lens of claim 11 wherein said first and second visually observable inversion markers are located adjacent diametrically opposed haptics.

* * * * *